United States Patent
Shelley et al.

(10) Patent No.: US 7,645,991 B1
(45) Date of Patent: Jan. 12, 2010

(54) METHOD OF USING IR SPECTROSCOPY TO DETERMINE PRESENCE OF METALLIC MATERIAL IN POLYMER COMPOSITE MATERIAL

(75) Inventors: Paul H. Shelley, Lakewood, WA (US); Gregory J. Werner, Puyallup, WA (US)

(73) Assignee: The Boeing Company, Chicago, IL (US)

( * ) Notice: Subject to any disclaimer, the term of this patent is extended or adjusted under 35 U.S.C. 154(b) by 41 days.

(21) Appl. No.: 12/188,016

(22) Filed: Aug. 7, 2008

(51) Int. Cl.
  *G01J 5/02* (2006.01)
  *G01J 3/28* (2006.01)
(52) U.S. Cl. .............. 250/339.07; 250/339.06; 250/339.08; 356/300; 356/301; 356/317
(58) Field of Classification Search ............ 250/339.06; 356/301–303, 317–320
See application file for complete search history.

(56) References Cited

U.S. PATENT DOCUMENTS 7,115,869 B2  10/2006  Shelley et al.

OTHER PUBLICATIONS

Lundergan, M. L., B. D. Zimmermann, B. Waterman, Mechanical and Optical Functionality of Field-Aged Optical Ground Wire Cable, Tech. Rep., Corning Inc., 1997.*

* cited by examiner

*Primary Examiner*—David P Porta
*Assistant Examiner*—Casey Bryant
(74) *Attorney, Agent, or Firm*—Tung & Associates

(57) ABSTRACT

An IR spectroscopic method of determining the presence or absence of metallic material embedded in polymer material including irradiating a surface of said polymer material and collecting at least one spectrum of reflected infrared energy from said surface of said over a spectrum of wavelengths including the near-infrared wherein said metallic material is at least partially absent in a affected condition; performing a multivariate comparison of said at least one spectrum with at least one reference spectrum to determine a change in reflectance of said at least one spectrum with respect to at least one reference spectrum wherein said metallic material is present in an unaffected condition; and, correlating the amount of said change in reflectance with the presence or absence of said metallic material embedded in said polymer material.

19 Claims, 4 Drawing Sheets

METHOD OF USING IR SPECTROSCOPY TO DETERMINE PRESENCE OF METALLIC MATERIAL IN POLYMER COMPOSITE MATERIAL

FIELD OF THE INVENTION

This disclosure generally relates to infrared (IR) spectroscopy measurement methods, and more particularly provides a method for performing non-destructive IR spectroscopy measurements of polymer composite materials to determine the presence or absence of embedded metallic material therein including evaluation of the condition of aircraft composite materials including interwoven wire fabric (IWWF).

BACKGROUND OF THE INVENTION

IR spectroscopy measurements may be useful for a variety of purposes including aerospace, automotive and industrial applications, as well as biological and bio-medical applications. For example, infrared (IR) radiation is readily absorbed or reflected by materials. As such, IR spectroscopy measurements may indicate a condition of a wide variety of organic as well as inorganic materials.

For example, resin-fiber composite material used in aircraft parts may degrade over time due to a variety of reasons including heat or ultraviolet (UV) light exposure, which may cause chemical degradation to a polymer structure to occur, thereby affecting the desired properties of the polymer structure including structural integrity such as strength of the composite material. In addition, resin-fiber composite material may be subjected to other sources of effect such as high intensity electrical discharges near or on the composite material such as caused by lightening strikes.

Polymer composite materials, such as resin-fiber composite materials may include embedded metal such as what is known in the art as interwoven wire fabric (IWWF) or expanded aluminum foil (EAF), which includes metal wire interwoven into the polymer composite material, which provides a degree of protection against lightening strikes near or on the material, by providing a low resistance path to diffuse the energy over a wider area.

High intensity electrical discharges, such as lightening strikes to a composite material including IWWF may result in the non-compliant properties of the IWWF within the composite material, resulting in a portion of the composite material that is non-compliant, including beyond the area of the material that is visibly struck by lightening. The missing IWWF must be replaced to provide electromagnetic event (EME) protection for the aircraft, including removing areas with IWWF loss and replacing the removed areas with good IWWF.

One non-destructive method in the prior art of ascertaining the condition of polymer composite material, such as the degree of UV or heat effect to composite materials, includes IR spectroscopy of the polymer composite material, and is outlined in U.S. Pat. No. 7,113,869, which is hereby incorporated by reference in its entirety.

Other non-destructive methods in the prior art include using IR spectroscopy to determine the amount of a chromated conversion coating on a metallic substrate (U.S. Pat. No. 6,794,631), determining the amount of an anodized coating on a metallic substrate, (U.S. Pat. No. 6,784,431), determining an amount of opaque coating on a substrate (U.S. Pat. No. 6,903,339), and determining an amount of heat exposure effect to a resin-fiber composite substrate (U.S. Pat. No. 7,115,869), all of which are fully incorporated herein by reference.

None of the above methods and associated devices, however, disclose a method that is suitable for performing IR spectroscopy to detect the presence or absence of embedded (integral) metallic material in a polymer composite material, and to thereby determine a degree of effect to the polymer composite material, particularly in a field environment, such as in aircraft maintenance.

Thus, there is a continuing need for improved IR non-destructive testing methods including a method that is suitable for performing IR spectroscopy to detect the presence or absence of embedded (integral) metallic material in a polymer composite material, and to thereby determine a degree of effect to the polymer composite material, particularly in a field environment, such as in an aircraft maintenance process.

Therefore it is an object of the invention to provide a method that is suitable for performing IR spectroscopy to detect the presence or absence of embedded (integral) metallic material in a polymer composite material, and to thereby determine a degree of effect to the polymer composite material, particularly in a field environment, such as in an aircraft maintenance process.

SUMMARY OF THE INVENTION

In one embodiment an IR spectroscopic method of determining the presence or absence of metallic material embedded in polymer material is provided, the method including An IR spectroscopic method of determining the presence or absence of metallic material embedded in polymer material including irradiating a surface of said polymer material and collecting at least one spectrum of reflected infrared energy from said surface of said over a spectrum of wavelengths including the near-infrared wherein said metallic material is at least partially absent in a affected condition; performing a multivariate comparison of said at least one spectrum with at least one reference spectrum to determine a change in reflectance of said at least one spectrum with respect to at least one reference spectrum wherein said metallic material is present in an unaffected condition; and, correlating the amount of said change in reflectance with the presence or absence of said metallic material embedded in said polymer material.

These and other objects, aspects and features of the invention will be better understood from a detailed description of the preferred embodiments of the invention which are further described below in conjunction with the accompanying Figures.

DETAILED DESCRIPTION OF THE PREFERRED EMBODIMENT

The present invention achieves the foregoing objects, aspects and features by providing a method of non-destructively determining the presence or absence of integral metallic material within a polymer composite (fiber-resin) material, such as the presence or absence of interwoven wire fabric (IWWF). Consequently, a degree of effect may be determined including the operational acceptability or unacceptability of the composite material. The method may be accomplished by making IR spectroscopy measurements using multivariate analysis with a portable IR Spectrometer, including on an aircraft part in the field.

Preferably, near-IR in the 1600-2400 nm range is used for making IR spectroscopy measurements in order to be able to "see' through (e.g., penetrate) overlying coatings of material, such as paint. For example, it has been found that mid-IR wavelengths cannot "see" through an overlying layer of paint, which may be present on the polymer composite material, such as aircraft parts.

It will be appreciated that although the invention is particularly explained with reference to using IR spectroscopy to determine a degree of effect as exemplified by an absence of the integral metallic material in polymer composite materials used in portions of aircraft, that the invention may additionally be advantageously used to determine in general, the presence or absence of a metallic material embedded in a polymer material at or near the surface of the polymer material, including underneath a coating of material, such as paint, on the surface of the polymer material.

In some embodiments of the invention, a portable hand-held spectrometer is preferably used to make IR spectroscopy measurements. By the term portable hand-held is meant an instrument that may be easily carried and picked up and move about to make IR spectroscopy measurements by an average person, e.g., has a weight of less than about 5 pounds and may be hand-held and aimed at a spot on the measurement surface.

Figure 1:
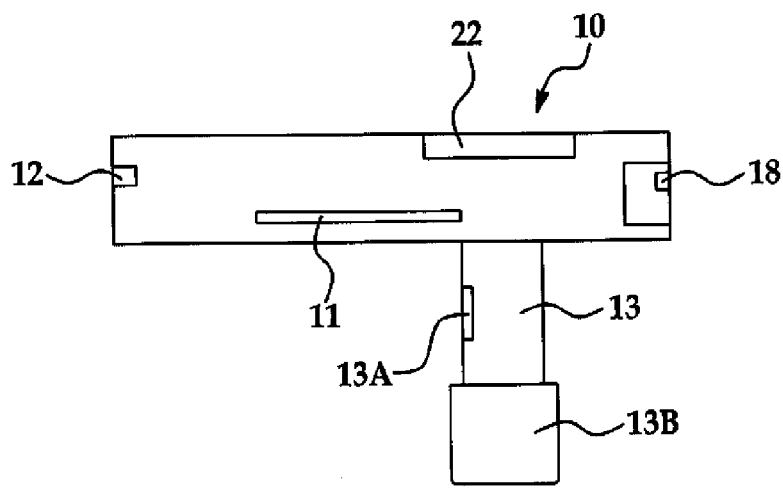
FIG. 1 is a schematic diagram of an exemplary hand-held portable IR spectrometer suitably used to make IR spectroscopy measurements according to an embodiment of the invention.

For example, referring to FIG. 1 is shown a side view of a suitable portable (handheld) IR spectrometer 10 which may be used to make IR spectroscopy measurements according to embodiments of the invention. The portable IR spectrometer 10 preferably has the capability to perform reflectance measurements, including diffuse reflectance measurements (also referred to as an external reflectance measurement). The portable spectrometer 10, as shown in FIG. 1 is preferably capable of IR spectroscopy measurements according to preferred embodiments of the invention over a wavelength range of about 1600 nanometers to about 2400 nanometers.

The portable IR spectrometer 10 also preferably includes a microprocessor and memory (e.g. micro-processor board 11) and may be interfaced (placed in communicated with) with other computing devices (e.g., USB port 18). The portable IR spectrometer 10 may be supplied power by one or more batteries (e.g., 13B in handle portion 13). The portable IR spectrometer 10 is preferably programmable and/or capable of accepting, storing, and executing preprogrammed instructions for carrying out IR spectroscopy measurements. The portable IR spectrometer 10 preferably has the capability to provide incident IR light (energy) and collect reflected IR spectra (e.g., through one or more IR transparent energy windows e.g., 12) over an operating wavelength range (e.g., 1600 nanometers to about 2400 nanometers) and to store the spectra and perform mathematical manipulation of the data comprising the spectra including multivariate analysis of the spectra.

The portable IR spectrometer 10 may include a triggering device e.g. 13A on handle portion 13 for triggering an IR spectroscopy or the IR spectroscopy may be alternately triggered by softkeys on an interactive LCD touchscreen 22. It will be appreciated that the portable IR spectrometer 10 may be of any suitable ergonomic shape to enhance the portability and ease of holding and manipulating the spectrometer to carryout field IR spectroscopy measurements.

In addition, suitable calibration background reference standard materials and wavelength reference standard materials may be provided for calibrating the IR spectrometer prior to performing IR spectroscopy measurements according to embodiments of the invention.

The portable IR spectrometer 10, or another IR spectrometer used to carry out IR spectroscopy measurements according to embodiments of the invention, preferably includes a computer processor capable of multivariate analysis of the IR spectra. For example, the IR spectrometer (or associated controller) preferably has the ability to mathematically and statistically correlate and determine changes in a plurality of variables (e.g., IR spectra including reflectance at a plurality of wavelengths) with respect to one or more reference IR spectra.

For example, in one embodiment, IR reference spectra may be collected from an aircraft part in a region that has the same overlying paint structure as a suspected bad area (e.g., IWWF affected by lightening strike), but which is a known to be a good area (e.g., known that IWWF is present in an unaffected condition). In addition, multivariate statistical approaches may be used to correlate the statistically determined changes in the plurality of variables (e.g., IR reflectance at one or more wavelengths) with one or more second variables or (e.g. a predicted distance to an unaffected area from a visibly affected area determined according to changes in the IR spectra).

There are many suitable multivariate techniques that may be used to make an IR spectroscopy measurement according to the present invention including, but not limited to, quantification methodologies, such as, partial least squares, principal component regression ("PCR"), linear regression, multiple linear regression, stepwise linear regression, ridge regression, radial basis functions, and the like.

In addition, suitable multivariate statistical approaches include classification methodologies, such as, linear discriminant analysis ("LDA"), cluster analysis (e.g., k-means, C-means, etc., both fuzzy and hard), and neural network ("NN") analysis.

Further, it will be appreciated that there are a multitude of data processing methods that may be suitably used in connection with suitable multivariate statistical approaches including smoothing, first and second derivatives, and peak enhancement methods.

For example, multivariate analysis of collected IR spectra may include the selection and clustering together of groups of wavelengths on which to perform a regression analysis to determine a corresponding change in the IR spectra (e.g., reflectance) from reference spectra (spectrum). In addition, the raw IR spectra may transformed into second IR spectra by taking first and/or second derivatives and performing smoothing and/or peak enhancement as well as carrying out regression analysis.

In addition, the multivariate analysis process may include collecting reference IR spectra (including calculated reflectance), which may serve as a baseline from which to determine relative changes by multivariate analysis in sample IR spectra. In addition, various processing methods as are known in the art may be used to form a single IR spectrum from a collection of a plurality of collected IR spectra, including various averaging techniques, for example to improve a signal to noise ratio.

Figure 2A:
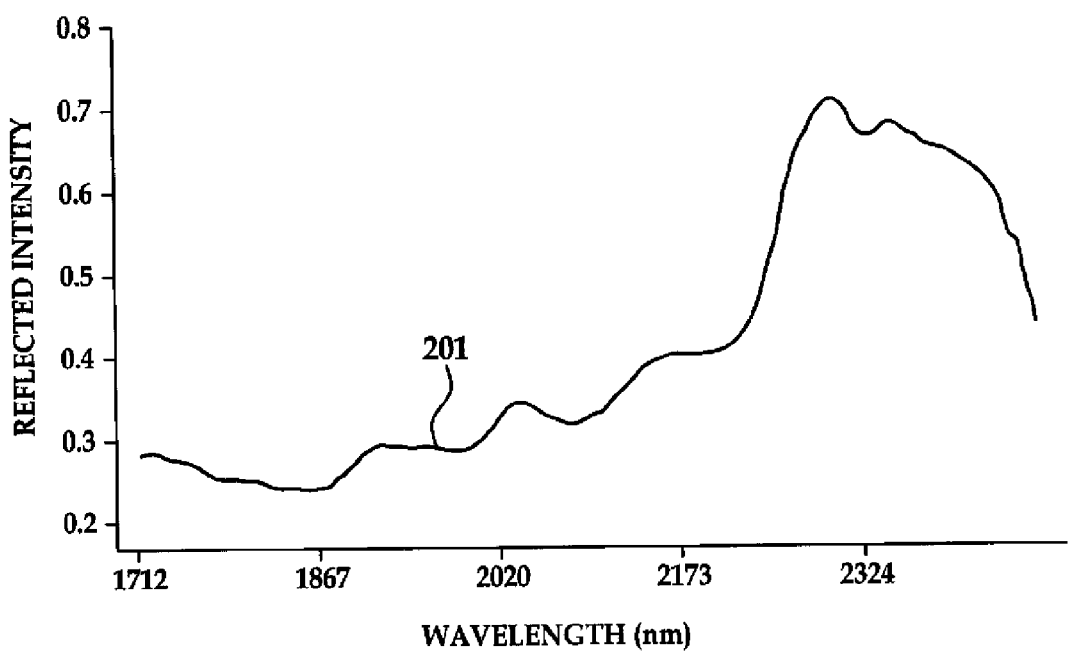
FIG. 2A is an exemplary raw IR spectrum according to an exemplary IR Spectroscopy measurement according to an embodiment of the invention.
Figure 2B:
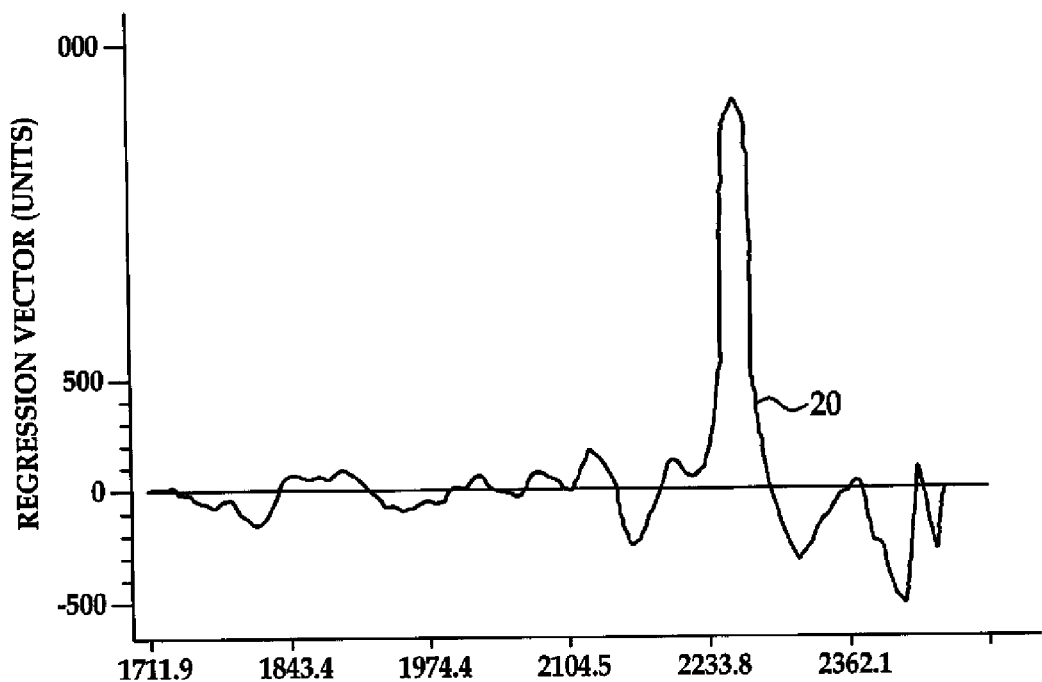
FIG. 2B is an exemplary IR spectrum subjected to multivariate analysis according to an exemplary IR Spectroscopy measurement according to an embodiment of the invention.

For example, referring to FIG. 2A is shown exemplary portion of a near-IR (1600-2400 nm) raw (as detected) IR spectrum 201 collected according to embodiments of the invention where Reflected Intensity is shown on the vertical axis and wavelength in nanometers is shown on the horizontal axis. Referring to FIG. 2B is shown an IR spectrum 202 following transformation of one or more raw IR spectra by multivariate analysis such as taking a first derivative, employing a smoothing algorithm, and determining a regression vector magnitude (vertical axis) (e.g., changes in reflectance compared to a reference IR spectrum).

Figure 2C:
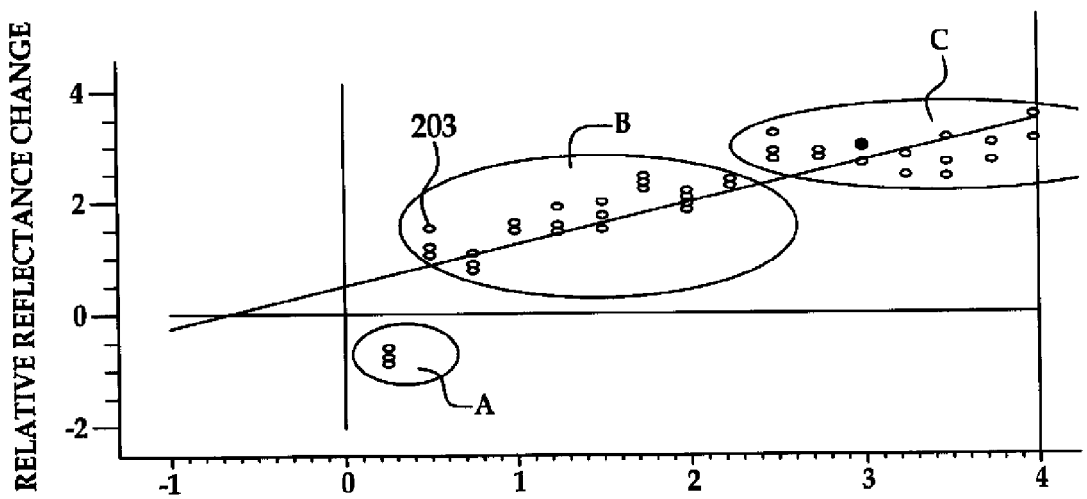
FIG. 2C is an exemplary multivariate regression analysis performed on several IR spectroscopy measurements according to an embodiment of the invention.

Referring to FIG. 2C is shown a correlation of the results of a plurality of IR spectroscopy measurements e.g., 203 (at selected wavelengths) and associated multivariate analysis (e.g., where vertical axis represents predicted distance from the strike and correlated by regression analysis (line R) with a known distance (horizontal axis) from the strike using a respective IR spectroscopy measurement from an edge of visible lightning strike effect. Thus, the exemplary regression analysis shown by line R can be correlated (e.g., area B) where an increasing vertical axis value correlates with a changing and decreasing level of effect (e.g., unaffected or relative presence of integral metallic material such as IWWF). In contrast, area C can be correlated with a relatively unaffected and unchanging IR reflectance spectra at distances greater than a threshold distance (e.g. 2.5 inches) from an edge of visible lightning strike effect where the IWWF is completely intact and unaffected (see also FIG. 3), while area A can be correlated with severe effect (e.g., complete absence of integral metallic material near edge of visible lightning strike effect).

Thus, by using a partial least square regression with respect to an actual distance from the visible edge of the lightening strike, and with respect to changes in the IR spectra, it can be predicted how far from the visible edge of the lightening strike where the IWWF is present in an unaffected condition and where it is present in a affected condition.

For example, by analyzing the data according to multivariate analysis (comparing sample IR spectra collected from a affected area of the polymer composite material with a reference spectra from an unaffected area of the polymer composite material), and correlating the data behavior (e.g., regression analysis) with a known condition of the polymer composite material (e.g., separately determined microscopic and/or X-ray analysis of the material for the presence or absence of IWWF), a determination as to the presence of affected composite material (IWWF fully or partially absent e.g., vaporized by lightening strike) or absence of such effect (IWWF present in unaffected condition) may be made, including forming a map of the affected area.

Figure 3:
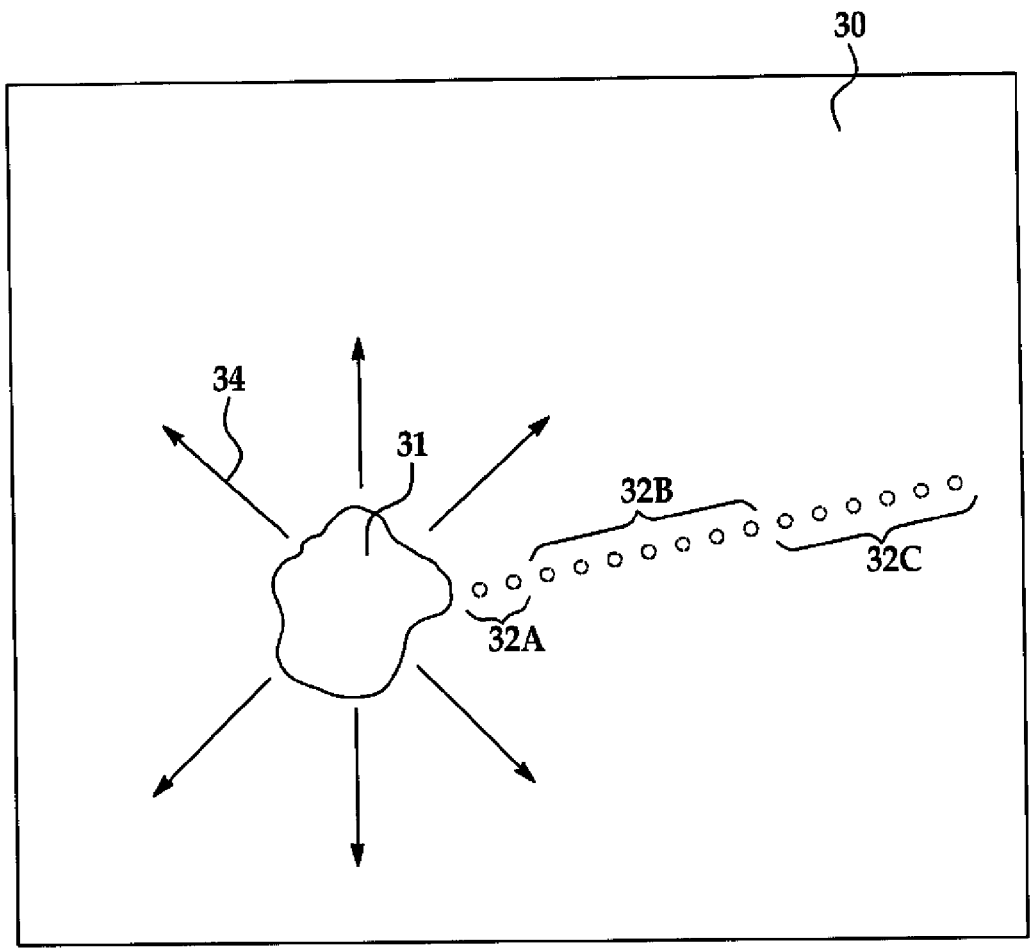
FIG. 3 is an exemplary IR spectroscopy measurement process showing several IR spectroscopy measurements taken over a distance from the edge of a lightning strike.

Referring to FIG. 3 is shown an exemplary surface 30 (e.g., painted) of a polymer (resin-fiber) composite material with IWWF (e.g., embedded in surface under paint), including an exemplary visibly affected (through paint) lightning strike area 31 together with a series of IR spectroscopy measurement areas measured according to embodiments of the invention (e.g., 32A, 32B, and 32C) taken at different distances from the visibly affected area 31. For example, spectroscopy measurement areas 32A represents severe effect (e.g., complete absence of IWWF within the polymer composite material), whereas spectroscopy measurement areas 32B represent steadily decreasing effect (e.g., as shown in area B in FIG. 2C), and spectroscopy measurement areas 32C represent no apparent effect to the IWWF embedded in the polymer material beyond a threshold distance from the visibly affected area 31 (e.g., as shown in area C in FIG. 2C).

It will be appreciated that the integral metallic material such as IWWF may be on or near the polymer composite material surface beneath coated or painted surfaces or on or near bare polymer composite material surfaces (fiber-resin) composite) material, and forms an integral portion of the fiber-resin composite material. It will be appreciated that an IR spectroscopy measurement process may include taking IR spectra at several radially extending directions e.g., 34 from the visibly affected lightning strike area 31, and that the IR spectroscopy measurements may be taken at random (e.g., randomly covering predefined selected distances and directions) or taken in sequence (sequentially covering predefined selected distances and directions). In a preferred measurement methodology, the sequence of measurements are predefined at increasing distances from the strike to assure a good (unaffected) area is included but where the individual spot measurements are made randomly to prevent spectrometer changes from affecting the measurement accuracy, such as where the spectrometer is warming up.

In an exemplary IR spectroscopy measurement process, the portable IR spectrometer 10 may used to make IR spectroscopy measurements over the wavelengths of about 1600 to 2400 nm. For example, the portable IR spectrometer 10 may be placed near or in contact with the surface (IR source/collection window may be recessed) to be measured and the size of the measured area will depend on the IR source window dimensions as well as the distance from the measurement surface.

Figure 4:
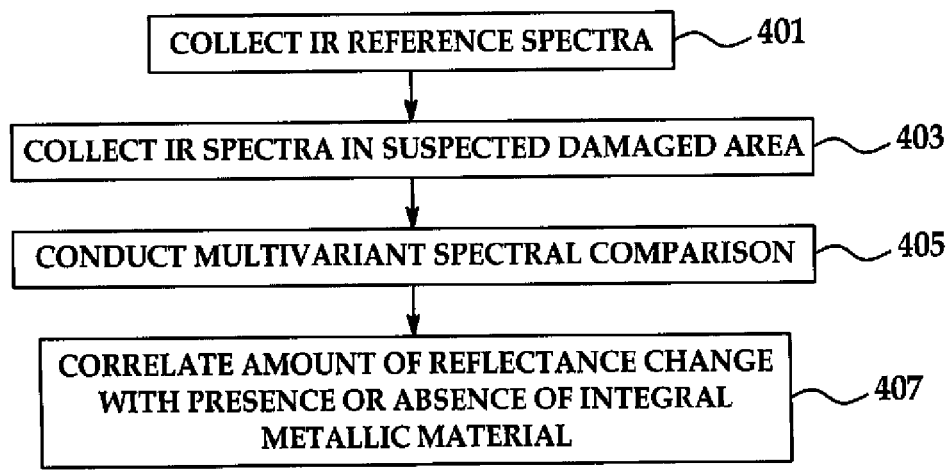
FIG. 4 is an exemplary process flow diagram including embodiments of the invention.

In an exemplary IR spectroscopy measurement process, referring to FIG. 4, in step 401 an operator collects an IR reference spectrum (or spectra). For example, the operator may collect the reference spectra from a reference sample (polymer composite material with IWWF present in an unaffected condition), preferably from an unaffected area where the polymer composite material to be measured is known to be unaffected but has the same overlying paint structure.

In step 403, the operator then collects sample IR spectra (spectrum) from an area suspected to be affected (e.g., suspected effect from lightening strike where IWWF is at least partially absent and/or in a affected condition).

In step 405, a multivariate spectral comparison is made including comparing sample IR spectra with the reference IR spectra to determine a relative change in the sample IR spectra, including a relative change in reflectance.

In step 405, the results of the multivariate analysis including an amount of reflectance change is correlated with the relative presence (e.g., unaffected) or absence (e.g. affected) of integral metallic material such as IWWF at predicted distances from a visibly affected area according to preferred embodiments. A determination may then be made whether the polymer composite material with IWWF is acceptable or unacceptable (must be repaired).

Figure 5:
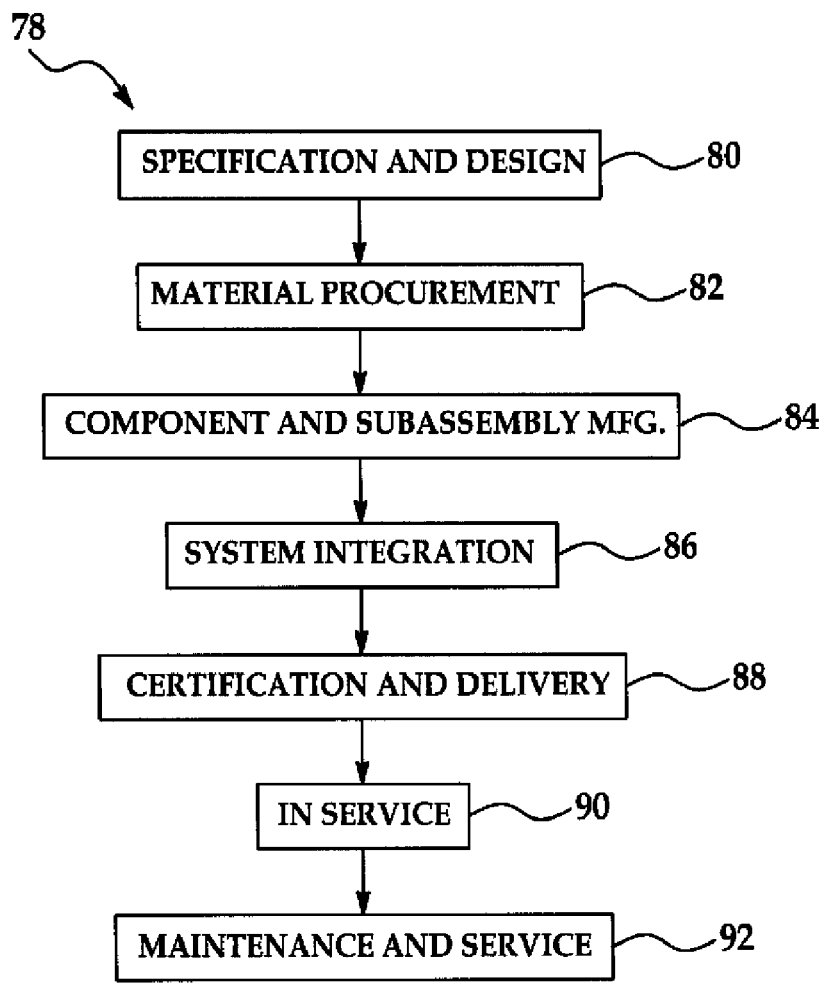
FIG. 5 is a flow diagram of an aircraft and service methodology.
Figure 6:
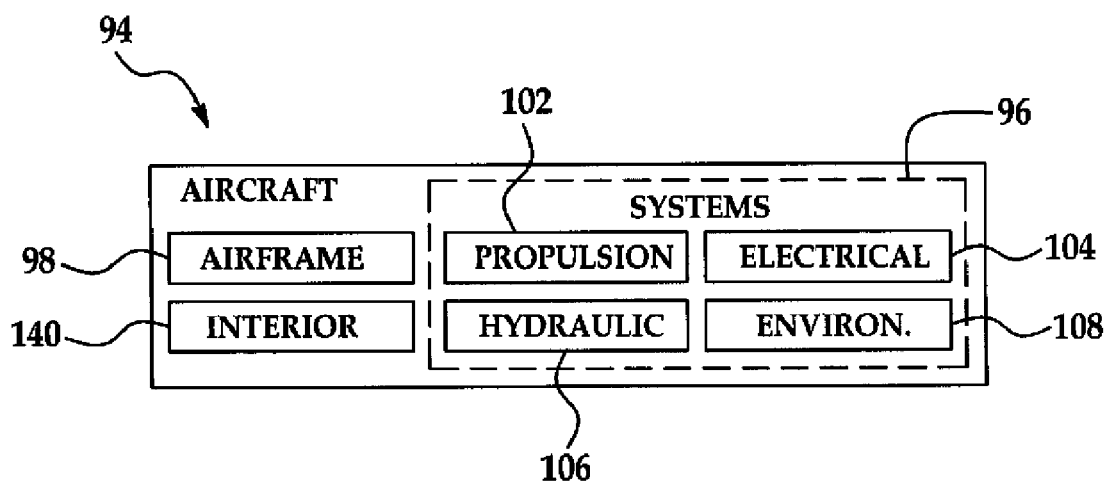
FIG. 6 is a block diagram of an aircraft.

Referring next to FIGS. 5 and 6, embodiments of the disclosure may be used in the context of an aircraft manufacturing and service method 78 as shown in FIG. 5 and an aircraft 94 as shown in FIG. 6. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 6, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. An IR spectroscopic method of determining the presence or absence of metallic material embedded in polymer material comprising:
    irradiating a surface of said polymer material and collecting at least one spectrum of reflected infrared energy from said surface of said polymer material over a spectrum of wavelengths comprising the near-infrared wherein said metallic material is at least partially absent in a affected condition;
    performing a multivariate comparison of said at least one spectrum with at least one reference spectrum to determine a change in reflectance of said at least one spectrum with respect to at least one reference spectrum wherein said metallic material is present in an unaffected condition; and,
    correlating the amount of said change in reflectance with the presence or absence of said metallic material embedded in said polymer material.

2. The method of claim 1, wherein multiple spectra are collected at different locations on said surface of said polymer material to map an area comprising the absence of said metallic material over said polymer material surface.

3. The method of claim 1, wherein said polymer material comprises a coating of paint on the surface.

4. The method of claim 1, wherein said polymer material comprises a composite resin-fiber material.

5. The method of claim 4, wherein said metallic material comprises metallic material integral with said composite resin-fiber material.

6. The method of claim 5, wherein said metallic material is selected from the group consisting of interwoven wire fabric (IWWF) and expanded aluminum foil (EAF).

7. The method of claim 1, wherein said step of irradiating a surface is preceded by irradiating said surface of said polymer material and collecting at least one reference spectrum comprising reflected infrared energy over said spectrum of wavelengths wherein said metallic material is present in an unaffected condition.

8. The method of claim 1, wherein said step of irradiating a surface is preceded by a calibration process comprising collecting reference spectra over said spectrum of wavelengths from a reference sample comprising a predetermined reflectance spectrum.

9. The method of claim 1, wherein said near infrared spectrum of wavelengths is from about 1600 to about 2400 nanometers.

10. The method of claim 1, wherein said step of irradiating is performed by a hand-held portable IR spectrometer.

11. An IR spectroscopic method of determining the presence or absence of metallic material embedded in a surface of a polymer composite material comprising:
    irradiating said surface of said polymer composite material and collecting at least one reference spectrum comprising reflected infrared energy over a spectrum of wavelengths comprising the near infrared wherein said metallic material is present in an unaffected condition;
    irradiating said surface of said polymer composite material and collecting at least one spectrum of reflected infrared energy from said surface over said spectrum of wavelengths wherein said metallic material is at least partially absent in a affected condition;
    performing a multivariate comparison of said at least one spectrum with at least one reference spectrum to determine a change in reflectance of said at least one spectrum with respect to at least one reference spectrum; and,
    correlating the amount of said change in reflectance with the presence or absence of said metallic material embedded in said surface of said polymer composite material.

12. The method of claim 11, wherein multiple spectra are collected at different locations on said surface of said polymer composite material to map an area comprising the absence of said metallic material embedded in said polymer composite material surface.

13. The method of claim 11, wherein said polymer material comprises a coating of paint on the surface.

14. The method of claim 11, wherein said polymer material comprises a composite resin-fiber material.

15. The method of claim 14, wherein said metallic material comprises metallic material integral with said composite resin-fiber material.

16. The method of claim 15, wherein said metallic material is selected from the group consisting of interwoven wire fabric (IWWF) and expanded aluminum foil (EAF).

17. The method of claim 11, wherein said near infrared spectrum of wavelengths is from about 1600 to about 2400 nanometers.

18. The method of claim 11, wherein said step of irradiating is performed by a hand-held portable IR spectrometer.

19. The method of claim 18, wherein said hand-held portable IR spectrometer detects said infrared energy reflected according to a diffuse reflectance measurement.

* * * * *